United States Patent
Jaffe et al.

(10) Patent No.: US 9,335,266 B2
(45) Date of Patent: May 10, 2016

(54) SYSTEM AND METHOD FOR CONTROLLED INTENSITY ILLUMINATION IN A BIOANALYSIS OR OTHER SYSTEM

(71) Applicant: Lumencor, Inc., Beaverton, OR (US)

(72) Inventors: Claudia B. Jaffe, Portland, OR (US); Steven M. Jaffe, Beaverton, OR (US); David Larsen, Beaverton, OR (US)

(73) Assignee: LUMENCOR, INC., Beaverton, OR (US)

( * ) Notice: Subject to any disclaimer, the term of this patent is extended or adjusted under 35 U.S.C. 154(b) by 307 days.

(21) Appl. No.: 13/874,645

(22) Filed: May 1, 2013

(65) Prior Publication Data

US 2013/0234047 A1 Sep. 12, 2013

Related U.S. Application Data

(63) Continuation of application No. 13/282,108, filed on Oct. 26, 2011, now Pat. No. 8,466,436, and a continuation-in-part of application No. 13/007,535, filed on Jan. 14, 2011, now Pat. No. 8,389,957.

(51) Int. Cl.

| | |
|---|---|
| *F21V 9/16* | (2006.01) |
| *G01J 1/58* | (2006.01) |
| *G01T 1/10* | (2006.01) |
| *G21H 3/02* | (2006.01) |
| *G21K 5/00* | (2006.01) |

(Continued)

(52) U.S. Cl.
CPC ............ *G01N 21/64* (2013.01); *F21V 23/0457* (2013.01); *G01N 21/6408* (2013.01); *G01N 21/6428* (2013.01); *G01N 21/6458* (2013.01); *H05B 33/0869* (2013.01); *G01N 2021/6419* (2013.01)

(58) Field of Classification Search
None
See application file for complete search history.

(56) References Cited

U.S. PATENT DOCUMENTS

| | | | |
|---|---|---|---|
| 1,998,054 | A | 4/1935 | McBurney |
| 3,313,337 | A | 4/1967 | Bernat |

(Continued)

FOREIGN PATENT DOCUMENTS

| | | |
|---|---|---|
| CA | 2 280 398 | 4/2000 |
| EP | 1 426 807 | 12/2003 |

(Continued)

OTHER PUBLICATIONS

International Search Report dated Dec. 31, 2008, Application No. PCT/US2008/072394, 10 pages.

(Continued)

*Primary Examiner* — Douglas W Owens
*Assistant Examiner* — Dedei K Hammond
(74) *Attorney, Agent, or Firm* — Tucker Ellis LLP (57) ABSTRACT

A system and method for controlled illumination in a bioanalysis or other system where excitation of fluorescent molecules is desirable. In an embodiment, an illumination system is described which can provide excitation light at a controlled intensity to provide quantitative results. In an embodiment, a solid state light engine is described which includes a plurality of color channels each providing light output suitable for exciting a fluorescent molecule, a light to frequency converter which receives a portion of the light output, a counter which maintains a count of a signal from the light to frequency converter, and a light intensity circuit, responsive to the counter, which adjusts the color channels to control the intensity of the light output.

22 Claims, 8 Drawing Sheets

(51) Int. Cl.
*H01J 65/00* (2006.01)
*G01N 21/64* (2006.01)
*H05B 33/08* (2006.01)
*F21V 23/04* (2006.01)

(56) References Cited

U.S. PATENT DOCUMENTS

| | | |
|---|---|---|
| 3,637,285 A | 1/1972 | Stewart |
| 3,759,604 A | 9/1973 | Thelen |
| 3,881,800 A | 5/1975 | Friesem |
| 3,982,151 A | 9/1976 | Ludovici |
| 4,003,080 A | 1/1977 | Maiman |
| 4,298,820 A | 11/1981 | Bongers |
| 4,371,897 A | 2/1983 | Kramer |
| 4,510,555 A | 4/1985 | Mori |
| 4,539,687 A | 9/1985 | Gordon |
| 4,602,281 A | 7/1986 | Nagasaki et al. |
| 4,626,068 A | 12/1986 | Caldwell |
| 4,642,526 A * | 2/1987 | Hopkins .................. 315/244 |
| 4,642,695 A | 2/1987 | Iwasaki |
| 4,644,141 A | 2/1987 | Hagen |
| 4,657,013 A | 4/1987 | Hoerenz et al. |
| 4,695,332 A | 9/1987 | Gordon |
| 4,695,732 A | 9/1987 | Ward |
| 4,695,762 A | 9/1987 | Berkstresser |
| 4,713,577 A | 12/1987 | Gualtieri |
| 4,724,356 A | 2/1988 | Daehler |
| 4,798,994 A | 1/1989 | Rijpers |
| 4,804,850 A | 2/1989 | Norrish et al. |
| 4,852,985 A | 8/1989 | Fujihara et al. |
| 4,937,661 A | 6/1990 | Van der Voort |
| 4,995,043 A | 2/1991 | Kuwata |
| 5,052,016 A | 9/1991 | Mahbobzadeh |
| 5,089,860 A | 2/1992 | Deppe |
| 5,109,463 A | 4/1992 | Lee |
| 5,126,626 A | 6/1992 | Iwasaki |
| 5,128,846 A | 7/1992 | Mills et al. |
| 5,137,598 A | 8/1992 | Thomas |
| 5,193,015 A | 3/1993 | Shanks |
| 5,200,861 A | 4/1993 | Moskovich |
| 5,226,053 A | 7/1993 | Cho |
| 5,231,533 A | 7/1993 | Gonokami |
| 5,233,372 A | 8/1993 | Matsumoto |
| 5,249,195 A | 9/1993 | Feldman |
| 5,285,131 A | 2/1994 | Muller |
| 5,289,018 A | 2/1994 | Okuda |
| 5,312,535 A | 5/1994 | Waska |
| 5,315,128 A | 5/1994 | Hunt |
| 5,332,892 A | 7/1994 | Li et al. |
| 5,345,333 A | 9/1994 | Greenberg |
| 5,363,398 A | 11/1994 | Glass |
| 5,416,342 A | 5/1995 | Edmond et al. |
| 5,416,617 A | 5/1995 | Loiseaux |
| 5,418,584 A | 5/1995 | Larson |
| 5,428,476 A | 6/1995 | Jensen |
| 5,469,018 A | 11/1995 | Jacobsen |
| 5,475,281 A | 12/1995 | Heijboer |
| 5,478,658 A | 12/1995 | Dodabalapur |
| 5,489,771 A | 2/1996 | Beach et al. |
| 5,493,177 A | 2/1996 | Muller |
| 5,500,569 A | 3/1996 | Blomberg |
| 5,542,016 A | 7/1996 | Kaschke |
| 5,616,986 A | 4/1997 | Jacobsen |
| 5,644,676 A | 7/1997 | Blomberg |
| 5,658,976 A | 8/1997 | Carpenter |
| 5,669,692 A | 9/1997 | Thorgersen |
| 5,671,050 A | 9/1997 | De Groot |
| 5,674,698 A | 10/1997 | Zarling |
| 5,690,417 A | 11/1997 | Polidor et al. |
| 5,715,083 A | 2/1998 | Takayama |
| 5,719,391 A | 2/1998 | Kain |
| 5,757,014 A | 5/1998 | Bruno |
| 5,781,338 A | 7/1998 | Kapitza et al. |
| 5,803,579 A | 9/1998 | Turnbull et al. |
| 5,804,919 A | 9/1998 | Jacobsen |
| 5,808,759 A | 9/1998 | Okamori et al. |
| 5,827,438 A | 10/1998 | Blomberg |
| 5,833,827 A | 11/1998 | Anazawa |
| 5,858,562 A | 1/1999 | Utsugi |
| 5,864,426 A | 1/1999 | Songer |
| 5,942,319 A | 8/1999 | Oyama |
| 5,955,839 A | 9/1999 | Jaffe |
| 5,984,861 A | 11/1999 | Crowley |
| 6,110,106 A | 8/2000 | MacKinnon et al. |
| 6,154,282 A | 11/2000 | Lilge et al. |
| 6,198,211 B1 | 3/2001 | Jaffe |
| 6,204,971 B1 | 3/2001 | Morris |
| 6,222,673 B1 | 4/2001 | Austin |
| 6,293,911 B1 | 9/2001 | Imaizumi et al. |
| 6,299,338 B1 | 10/2001 | Levinson |
| 6,304,584 B1 | 10/2001 | Krupke |
| 6,366,383 B1 | 4/2002 | Roeder |
| 6,392,341 B2 | 5/2002 | Jacobsen |
| 6,404,127 B2 | 6/2002 | Jacobsen |
| 6,404,495 B1 | 6/2002 | Melman |
| 6,422,994 B1 | 7/2002 | Kaneko et al. |
| 6,444,476 B1 | 9/2002 | Morgan |
| 6,513,962 B1 | 2/2003 | Mayshack et al. |
| 6,517,213 B1 | 2/2003 | Fujita et al. |
| 6,529,322 B1 | 3/2003 | Jones |
| 6,542,231 B1 | 4/2003 | Garrett |
| 6,544,734 B1 | 4/2003 | Briscoe |
| 6,594,075 B1 | 7/2003 | Kanao et al. |
| 6,608,332 B2 | 8/2003 | Shimizu |
| 6,614,161 B1 | 9/2003 | Jacobsen |
| 6,614,179 B1 | 9/2003 | Shimizu et al. |
| 6,637,905 B1 | 10/2003 | Ng |
| 6,642,652 B2 | 11/2003 | Collins |
| 6,649,432 B1 | 11/2003 | Eilers |
| 6,674,575 B1 | 1/2004 | Tandler et al. |
| 6,680,569 B2 | 1/2004 | Mueller-Mach et al. |
| 6,685,341 B2 | 2/2004 | Ouderkirk et al. |
| 6,690,467 B1 | 2/2004 | Reel |
| 6,717,353 B1 | 4/2004 | Mueller |
| 6,747,710 B2 | 6/2004 | Hall |
| 6,791,259 B1 | 9/2004 | Stokes et al. |
| 6,791,629 B2 | 9/2004 | Moskovich |
| 6,795,239 B2 | 9/2004 | Tandler et al. |
| 6,843,590 B2 | 1/2005 | Jones |
| 6,869,206 B2 | 3/2005 | Zimmerman et al. |
| 6,870,165 B2 | 3/2005 | Amirkhanian |
| 6,926,848 B2 | 8/2005 | Le Mercier |
| 6,958,245 B2 | 10/2005 | Seul et al. |
| 6,960,872 B2 | 11/2005 | Beeson et al. |
| 6,981,970 B2 | 1/2006 | Karni |
| 6,991,358 B2 | 1/2006 | Kokogawa |
| 6,995,355 B2 | 2/2006 | Rains, Jr. et al. |
| 7,009,211 B2 | 3/2006 | Eilers |
| 7,011,421 B2 | 3/2006 | Hulse et al. |
| 7,035,017 B2 | 4/2006 | Tadic-Galeb |
| 7,083,610 B1 | 8/2006 | Murray |
| 7,141,801 B2 | 11/2006 | Goodwin |
| 7,153,015 B2 | 12/2006 | Brukilacchio |
| 7,192,161 B1 | 3/2007 | Cleaver et al. |
| 7,205,048 B2 | 4/2007 | Naasani |
| 7,208,007 B2 | 4/2007 | Nightingale et al. |
| 7,211,833 B2 | 5/2007 | Slater, Jr. et al. |
| 7,239,449 B2 | 7/2007 | Leitel et al. |
| 7,300,175 B2 | 11/2007 | Brukilacchio |
| 7,316,497 B2 | 1/2008 | Rutherford et al. |
| 7,384,797 B1 | 6/2008 | Blair |
| 7,416,313 B2 | 8/2008 | Westphal et al. |
| 7,422,356 B2 | 9/2008 | Hama et al. |
| 7,427,146 B2 | 9/2008 | Conner |
| 7,445,340 B2 | 11/2008 | Conner |
| 7,467,885 B2 | 12/2008 | Grotsch et al. |
| 7,488,088 B2 | 2/2009 | Brukilacchio |
| 7,488,101 B2 | 2/2009 | Brukilacchio |
| 7,498,734 B2 | 3/2009 | Suehiro et al. |
| 7,540,616 B2 | 6/2009 | Conner |
| 7,633,093 B2 | 12/2009 | Blonder et al. |
| 7,709,811 B2 | 5/2010 | Conner |
| 7,746,560 B2 | 6/2010 | Yamazaki |
| 7,832,878 B2 | 11/2010 | Brukilacchio |

(56) References Cited

U.S. PATENT DOCUMENTS

| | | | |
|---|---|---|---|
| 7,837,348 | B2 | 11/2010 | Narendran et al. |
| 7,846,391 | B2 | 12/2010 | Jaffe et al. |
| 7,854,514 | B2 | 12/2010 | Conner |
| 7,857,457 | B2 | 12/2010 | Rutherford et al. |
| 7,898,665 | B2 | 3/2011 | Brukilacchio et al. |
| 8,029,142 | B2 | 10/2011 | Conner |
| 8,098,375 | B2 | 1/2012 | Brukilacchio |
| 8,242,462 | B2 | 8/2012 | Jaffe et al. |
| 8,258,487 | B1 | 9/2012 | Jaffe et al. |
| 8,263,949 | B2 | 9/2012 | Jaffe et al. |
| 8,279,442 | B2 | 10/2012 | Brukilacchio et al. |
| 8,309,940 | B2 | 11/2012 | Jaffe et al. |
| 8,389,957 | B2 | 3/2013 | Jaffe et al. |
| 2001/0055208 | A1 | 12/2001 | Kimura |
| 2002/0109844 | A1 | 8/2002 | Christel et al. |
| 2002/0127224 | A1 | 9/2002 | Chen |
| 2003/0044160 | A1 | 3/2003 | Jonese et al. |
| 2003/0095401 | A1 | 5/2003 | Hanson et al. |
| 2003/0127609 | A1 | 7/2003 | El-Hage et al. |
| 2003/0160151 | A1 | 8/2003 | Zarate et al. |
| 2003/0230728 | A1* | 12/2003 | Dai et al. .............. 250/458.1 |
| 2003/0233138 | A1 | 12/2003 | Spooner |
| 2004/0090600 | A1 | 5/2004 | Blei |
| 2004/0247861 | A1 | 12/2004 | Naasani |
| 2004/0264185 | A1 | 12/2004 | Grotsch et al. |
| 2005/0062404 | A1 | 3/2005 | Jones et al. |
| 2005/0116635 | A1 | 6/2005 | Walson et al. |
| 2005/0146652 | A1 | 7/2005 | Yokoyama et al. |
| 2005/0152029 | A1* | 7/2005 | Endo ..................... 359/385 |
| 2005/0184651 | A1 | 8/2005 | Cheng |
| 2005/0201899 | A1 | 9/2005 | Weisbuch |
| 2005/0248839 | A1 | 11/2005 | Yamaguchi |
| 2005/0260676 | A1 | 11/2005 | Chandler |
| 2005/0263679 | A1 | 12/2005 | Fan |
| 2006/0002131 | A1 | 1/2006 | Schultz et al. |
| 2006/0030026 | A1 | 2/2006 | Garcia |
| 2006/0060872 | A1 | 3/2006 | Edmond et al. |
| 2006/0060879 | A1 | 3/2006 | Edmond |
| 2006/0097136 | A1* | 5/2006 | Baxter et al. ........... 250/214 AL |
| 2006/0114960 | A1 | 6/2006 | Snee |
| 2006/0170931 | A1 | 8/2006 | Guo |
| 2006/0237658 | A1 | 10/2006 | Waluszko |
| 2006/0282137 | A1 | 12/2006 | Nightingale et al. |
| 2007/0053184 | A1 | 3/2007 | Brukilacchio |
| 2007/0053200 | A1 | 3/2007 | Brukilacchio |
| 2007/0058389 | A1 | 3/2007 | Brukilacchio |
| 2007/0064202 | A1 | 3/2007 | Moffat et al. |
| 2007/0086006 | A1 | 4/2007 | Ebersole et al. |
| 2007/0126017 | A1 | 6/2007 | Krames et al. |
| 2007/0211460 | A1 | 9/2007 | Ravkin |
| 2007/0253733 | A1 | 11/2007 | Fey |
| 2007/0262731 | A1 | 11/2007 | Jaffar et al. |
| 2007/0279914 | A1 | 12/2007 | Rutherford et al. |
| 2007/0279915 | A1 | 12/2007 | Rutherford et al. |
| 2007/0280622 | A1 | 12/2007 | Rutherford et al. |
| 2007/0281322 | A1 | 12/2007 | Jaffe et al. |
| 2007/0284513 | A1 | 12/2007 | Fan |
| 2007/0297049 | A1 | 12/2007 | Schadwinkel et al. |
| 2008/0079910 | A1 | 4/2008 | Rutherford et al. |
| 2008/0224024 | A1 | 9/2008 | Ashdown |
| 2008/0291446 | A1 | 11/2008 | Smith |
| 2008/0309929 | A1 | 12/2008 | Christiansen et al. |
| 2009/0122533 | A1 | 5/2009 | Brukilacchio |
| 2009/0196046 | A1 | 8/2009 | Rutherford et al. |
| 2009/0268461 | A1 | 10/2009 | Deak et al. |
| 2010/0188017 | A1 | 7/2010 | Brukilacchio |
| 2010/0237783 | A1* | 9/2010 | Dupre et al. .............. 315/149 |
| 2011/0044858 | A1 | 2/2011 | Jaffe et al. |
| 2012/0106192 | A1 | 5/2012 | Brukilacchio |
| 2012/0181936 | A1 | 7/2012 | Jaffe et al. |
| 2012/0181937 | A1 | 7/2012 | Jaffe et al. |
| 2012/0238472 | A1 | 9/2012 | Jaffe et al. |
| 2012/0252704 | A1 | 10/2012 | Jaffe et al. |
| 2012/0307514 | A1 | 12/2012 | Brukilacchio et al. |
| 2013/0099135 | A1 | 4/2013 | Jaffe et al. |

FOREIGN PATENT DOCUMENTS

| | | |
|---|---|---|
| GB | 0943756 | 12/1963 |
| GB | 2 000 173 A | 1/1979 |
| JP | 02-804873 | 7/1998 |
| JP | 2005-195485 | 7/2005 |
| JP | 2005-243973 | 9/2005 |
| JP | 2006-049814 | 2/2006 |
| JP | 2007-133435 | 5/2007 |
| JP | 2008139796 | 6/2008 |
| KR | 10-2006-0055934 | 5/2006 |
| KR | 10-2006-0089104 | 8/2006 |
| WO | WO 02/080577 | 10/2002 |
| WO | WO 2004/114053 | 12/2004 |
| WO | WO 2006/067885 | 6/2006 |
| WO | WO 2006/120586 | 11/2006 |

OTHER PUBLICATIONS

International Search Report for PCT/US2010021843 dated Aug. 19, 2010, 9 pages.

Extended European Search Report for PCT/US2008072394 dated Oct. 7, 2011, 9 pages.

International Search Report dated Jun. 19, 2012 for Application No. PCT/US2011/063030, 11 pages.

Extended European Search Report for PCT/US2007/069490 dated Oct. 26, 2012, 8 pages.

Albrecht, M., et al., "Scintillators and Wavelength Shifters for the Detection of Ionizing Radiation," Astroparticle, Particle and Space Physics, Detectors and Medical Physics Applications, ICATPP-8, M. Barone, et al., Eds, World Scientific, pp. 502-511 (2004).

Da-Lite Screen Company, Inc., www.da-lite.com, 46 pages website downloads as of Oct. 8, 1998.

DDS™ Rear Projection Screens, LORS™ Reflection Screens, ©1998 Physical Optics Corporation, Torrance, CA, 2 pages.

Deck, L., et al., "Two color light-emitting-diode source for high precision phase-shifting interferometry", Optics Letters, vol. 18, No. 22, Nov. 15, 1993, pp. 1899-1901.

Depp, S.W., et al., "Flat Panel Displays," Scientific American, pp. 90-97, Mar. 1993.

Flor-Henry, M., et al., "Use of a Highly Sensitive Two-Dimensional Luminescence Imaging System to Monitor Endogenous Bioluminescence in Plant Leaves," BMC Plant Biology, vol. 4, No. 19, Nov. 2004.

Hamberg, I. and Granqvist, C.G., "Evaporated Sn-doped $In_2O_3$ films: Basic optical properties and applications to energy-efficient windows," Journal of Applied Physics, vol. 60, No. 11, pp. R123-R159, Dec. 1, 1986.

Handbook of Optics, vol. 1—Fundamentals, Techniques, and Design, Second Edition, Chapter 42: Optical Properties of Films and Coatings, J.A. Dobrowolski, pp. 42.3-42.25, McGraw-Hill, Inc., © 1995.

Haroche, S., et al., "Cavity Quantum Electrodynamics," Scientific American, pp. 54-62, Apr. 1993.

Hecht, Jeff, "Diverse fiberoptic systems require varied sources," Laser Focus World, vol. 36, No. 1, pp. 155-161, Jan. 2000.

Hemingway, D.J. and Lissberger, P.H., "Effective Refractive Indices of Metal-Dielectric Interference Filters," Applied Optics, vol. 6, No. 3, pp. 471-476, Mar. 1967.

Hinds, E.A., "Spectroscopy of Atoms in a Micron-Sized Cavity," (date and periodical title unknown), pp. 18-19.

Holloway, R.J. and Lissberger, P.H., "The Design and Preparation of Induced Transmission Filters," Applied Optics, vol. 8, No. 3, pp. 653-660, Mar. 1969.

Huo, D.T.C., et al., "Reticulated Single-Crystal Luminescent Screen," J. Electrochem. Soc., vol. 133, No. 7, pp. 1492-1497, Jul. 1986.

Jenmar Visual Systems, Sunnyvale, CA, 4 pages, no date, but at least as early as Oct. 15, 1998.

Landau, B.V. and Lissberger, P.H., "Theory of Induced-Transmission Filters in Terms of the Concept of Equivalent Layers," Journal of the Optical Society of America, vol. 62, No. 11, pp. 1258-1264, Nov. 1972.

(56) References Cited

OTHER PUBLICATIONS

Launer, Herbert F., "Exposure Meter for Precision Light Dosage", The Review of Scientific Instruments, vol. 20, No. 2, Feb. 1949, pp. 103-109.

Lissberger, P.H., "Coatings with Induced Transmission," Applied Optics, vol. 20, No. 1, pp. 95-103, Jan. 1, 1981.

Mauch, R.H., et al., "Optical Behaviour of Electroluminescent Devices," Springer Proceedings in Physics, vol. 38, Electroluminescence, © Springer-Verlag Berlin, Heidelberg, pp. 291-295 (1989).

Morgan, C. G., et al., "New Approaches to Lifetime-Resolved Luminescence Imaging", Journal of Fluorescence, vol. 7, No. 1, 1997, pp. 65-73.

Pelletier, E. and Macleod, H.A., "Interference Filters with Multiple Peaks," Journal of the Optical Society of America, vol. 72, No. 6, pp. 683-687, Jun. 1982.

Plasma Display Manufacturers of the American Display Consortium, "Recommended Research Topics on Plasma Display for the DARPA Sponsored Phosphor Center of Excellence," pp. 1-2, Mar. 24, 1993.

Poelman, D., et al., "Spectral Shifts in Thin Film Electroluminescent Devices: An Interference Effect," J. Phys. D: Appl. Phys., vol. 25, pp. 1010-1013 (1992).

Schott Glass Technologies, Inc., Schott Total Customer Care, Contrast Enhancement Filters, Duryea, PA, 6 pages, Jan. 1998.

Schubert, E.F., et al., "Giant Enhancement of Luminescence Intensity in Er-doped $Si/SiO_2$ Resonant Cavities," Appl. Phys. Lett. vol. 61, No. 12, pp. 1381-1383, Sep. 21, 1992.

Stewart Filmscreen Corporation®, www.stewartfilm.com, 34 pages website downloads as of Oct. 8, 1998.

Tuenge, R.T., "Current Status of Color TFEL Phosphors," Electroluminescence—Proceedings of the Sixth International Workshop on Electroluminescence, El Paso, Tex., pp. 173-177, May 1992.

Vlasenko, N. A., et al., "Interference of Luminescent Emission from an Evaporated Phosphor," Opt. Spect., vol. 11, pp. 216-219 (1961).

Vlasenko, N. A., et al., "Investigation of Interference Effects in Thin Electroluminescent ZnS-Mn Films," Opt. Spect., vol. 28, pp. 68-71 (1970).

Whitaker, Jerry C., "Electronic Displays: Technology, Design, and Applications," McGraw-Hill, Inc., pp. 185-192 (1994).

World Watch, Photonics Spectra, "IR Reflective Coating Boosts Bulb's Output, Recycling of IR Energy Saves Power, Cuts Costs" pp. 40-41, Jan. 1991.

Yamamoto, Y., et al., "Optical Processes in Microcavities," Physics Today, pp. 66-73, Jun. 1993.

Yokoyama, H., "Physics and Device Applications of Optical Microcavities," Science, vol. 256, pp. 66-70, Apr. 3, 1992.

Young, L., "Multilayer Interference Filters with Narrow Stop Bands," Applied Optics, vol. 6, No. 2, pp. 297-312, Feb. 1967.

European Patent Office, 80298 Munich Germany, Extended European Search Report dated Oct. 15, 2014 for Application No. 11855826.1, 6 pages.

TAOS, Texas Advanced Optoelectronic Solutions®, "TSL230RD, TSL230ARD, TSL230BRD Programmable Light-To-Frequency Converters", TAOS054P—Copyright © Oct. 2007, TAOS Inc., 14 pages.

\* cited by examiner

SYSTEM AND METHOD FOR CONTROLLED INTENSITY ILLUMINATION IN A BIOANALYSIS OR OTHER SYSTEM

CLAIM OF PRIORITY

This application is a continuation of U.S. patent application Ser. No. 13/282,108, filed Oct. 26, 2011 entitled "SYSTEM AND METHOD FOR METERED DOSAGE ILLUMINATION IN A BIOANALYSIS OR OTHER SYSTEM" and which application is a continuation-in-part of U.S. patent application Ser. No. 13/007,535, filed Jan. 14, 2011, now U.S. Pat. No. 8,389,957, issued Mar. 5, 2013, entitled "SYSTEM AND METHOD FOR METERED DOSAGE ILLUMINATION IN A BIOANALYSIS OR OTHER SYSTEM", which is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

The invention is generally related to light sources, and bioanalytics or bioanalysis, and is particularly related to a system and method for metered dosage illumination in a bioanalysis or other system, including applications in research and development; and in clinical and diagnostic arenas.

BACKGROUND

Bioanalytics or bioanalysis is the analysis of biological samples. Bioanalysis systems often use light to excite fluorescence from molecular tags in a sample (referred to herein as fluorescent tags or fluors). Fluors may be exogenous, as in the case of fluorescently labeled immunochemical tags that recognize subcellular structure and bind to impose fluorescent labeling; or endogenous, as in the case of genetically modified cells in which fluorescent proteins for example are expressed in order to impart specific fluorescent signals within a living cell. Particularly in fields such as fluorescence imaging, gene expression analysis, various types of sequencing, high resolution fluorescence microscopy, fluorescence life time measurements, and high content screening, it is necessary to be able to measure the amount of fluorescence and compare that amount to other measurements. This means the excitation light flux must generally be measured for each illumination exposure or fluorescence excitation event. To monitor biological events, it is necessary to be able to measure specific biological activity with often sub-millisecond exposure times. Excitation and detection must occur rapidly, such that the illumination must be generally switched on and off within a time period that is at most one-tenth of the duration of the minimum exposure time. Additionally, fluors can be temporarily or permanently photo-bleached, and biological samples can be otherwise damaged by the illumination light—a process known as phototoxicity. In order to minimize perturbation of the fluors due to photo-bleaching, and photo-damage to the biological samples, it is generally desired to minimize the light flux or dosage within the constraints of the signal-to-noise (S/N) requirements of that particular bioanalysis system. These are the general areas that embodiments of the invention are intended to address.

SUMMARY

Described herein is a system and method for metered dosage illumination in a bioanalysis or other system. In accordance with an embodiment, an illumination system or subsystem is described that can provide optimized amounts of excitation light within the short exposure times necessary to measure fast biological activity. The amount of light can be precisely measured to provide quantitative results. The light flux can also be precisely controlled to generate only a prescribed minimum amount of light, in order to reduce adverse lighting effects on both fluors and samples. Although the examples herein illustrate the providing of metered dosage illumination in the context of a bioanalysis system, the techniques can be similarly used to provide metered dosage illumination in the context of other types of system. In accordance with various embodiments, the technique is particularly useful in any quality-control, analysis, or assessment-based environment. Typical research and development applications can include quality control, instrument calibration, and light output standardization; while clinical and diagnostics applications can include clinical monitoring, bioassay calibration and control for diagnostics, treatment and or therapeutic evaluation.

DETAILED DESCRIPTION

As described above, in the context of bioanalysis, it is often required that an excitation light flux be measured for each illumination exposure or fluorescence excitation event; or that the illumination be switched on and off within an appropriately brief time period; or that the light flux or dosage be minimized within the constraints of the signal-to-noise (S/N) requirements of the particular bioanalysis system.

To address this, described herein is a system and method for metered dosage illumination in a bioanalysis or other system. In accordance with an embodiment, an illumination system or subsystem is described that can provide optimized amounts of excitation light within the short exposure times necessary to measure fast biological activity. The amount of light can be precisely measured to provide quantitative results. The light flux can also be precisely controlled to generate only a prescribed minimum amount of light, in order to reduce adverse lighting effects on both fluors and samples. In accordance with various embodiments, the technique is particularly useful in any quality-control, analysis, or assessment-based environment. Typical research and development applications can include quality control, instrument calibration, and light output standardization; while clinical and diagnostics applications can include clinical monitoring, bioassay calibration and control for diagnostics, treatment and or therapeutic evaluation.

Figure 1:
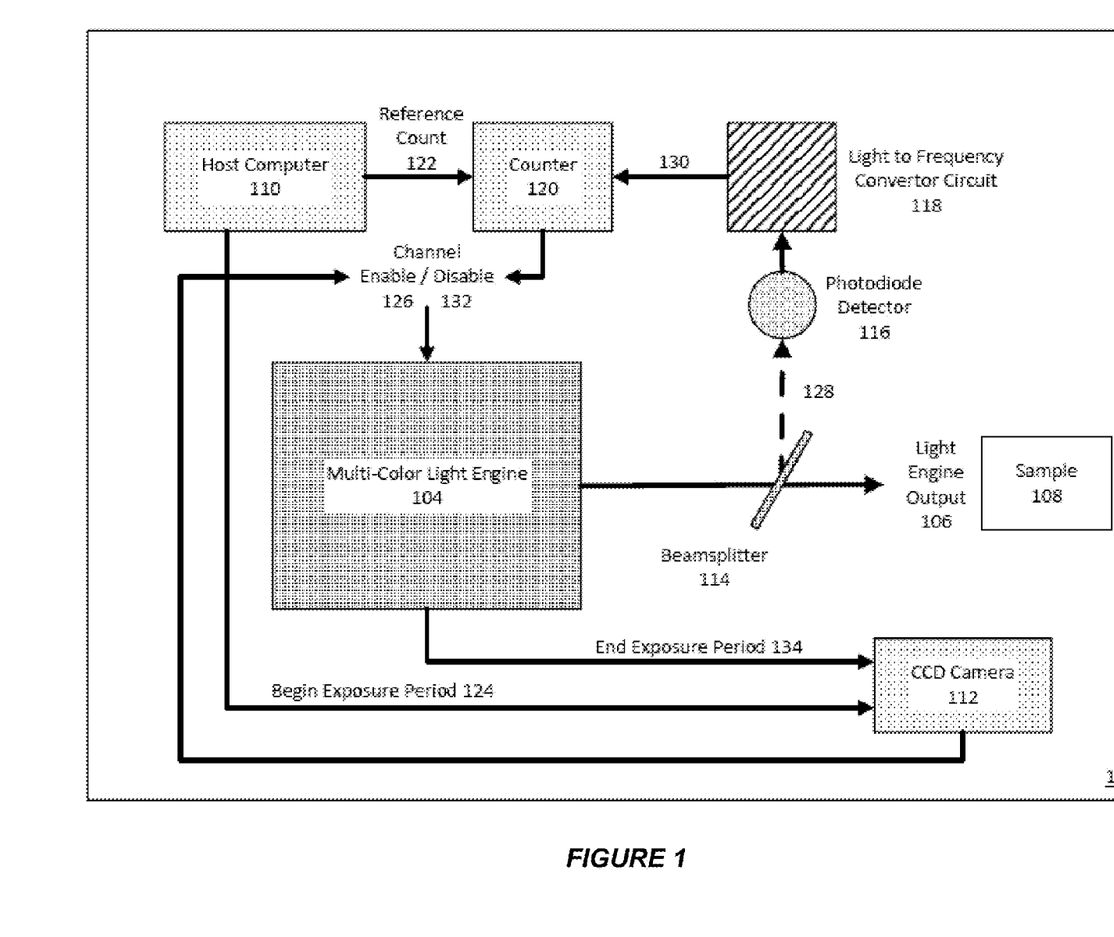
FIG. 1 illustrates a system for metered dosage illumination, in accordance with an embodiment.

FIG. 1 illustrates a system for metered dosage illumination, in accordance with an embodiment. As shown in FIG. 1, in accordance with an embodiment, the system 102 comprises a multi-color light engine 104 that can provide a plurality of different colors of light as a light output 106, to excite various fluorescent markers in a sample 108. An example of such a light engine can be the SPECTRA series of light engines supplied by Lumencor, Inc.

A host computer 110 generates an analysis protocol, including providing a dosage for each of the plurality of colors, and receiving feedback data from a camera 112. In accordance with an embodiment, the dosage can be in the form of a reference count that represents the amount of light flux per exposure period for each color provided by the light engine.

The camera is configured to detect fluorescence from the sample.

A beamsplitter 114 directs a portion of the light engine output, from the light engine, to a photodiode detector 116. A light-to-frequency converter 118 converts the detector output to a pulse train 130, the frequency of which is proportional to the light flux. A microprocessor-based counter 120 counts the pulse train, for each color, and compares the ongoing count to the reference count or preset dosage for each color.

Depending on the particular implementation, the above components can be provided as part of a complete system; or alternatively some or all of the above components can be provided as part of an illumination subsystem. For example, in accordance with an embodiment, the multi-color light engine, beamsplitter, photodiode detector, light-to-frequency converter, and microprocessor-based counter components can be provided as an illumination subsystem intended for use with a separately-provided host computer and camera.

In accordance with an embodiment, during operation of the system, the host computer downloads a reference count 122 for each color to the microprocessor-based counter. For each exposure period, the computer triggers the camera to begin an exposure period 124. The camera then sends an enable message or otherwise enables 126 the light engine, to turn on the appropriate color, and begins integrating the fluorescence. A portion of the light engine output 128, as directed by the beamsplitter, is monitored by the photodiode detector. The detector's output is converted to the pulse train that is then counted by the counter. When the counter reaches the reference count, it disables 132 the color channel currently on or provided by the light engine. Simultaneously, another trigger 134 is sent to the camera, ending the current exposure period.

The above approach avoids the latency inherent in any non-real-time operating systems. In accordance with an embodiment, additional circuitry can be provided to determine which color should be activated, and eliminate any delay inherent in the light engine turning on a color channel. An alternative approach is for the computer to turn on each color directly in conjunction with starting the camera's exposure period. In yet other embodiments, the procedure described above can be modified to suit the particular needs of the system (such as its use in quantitative analyses, or temporally fast analyses, as described below).

Figure 2:
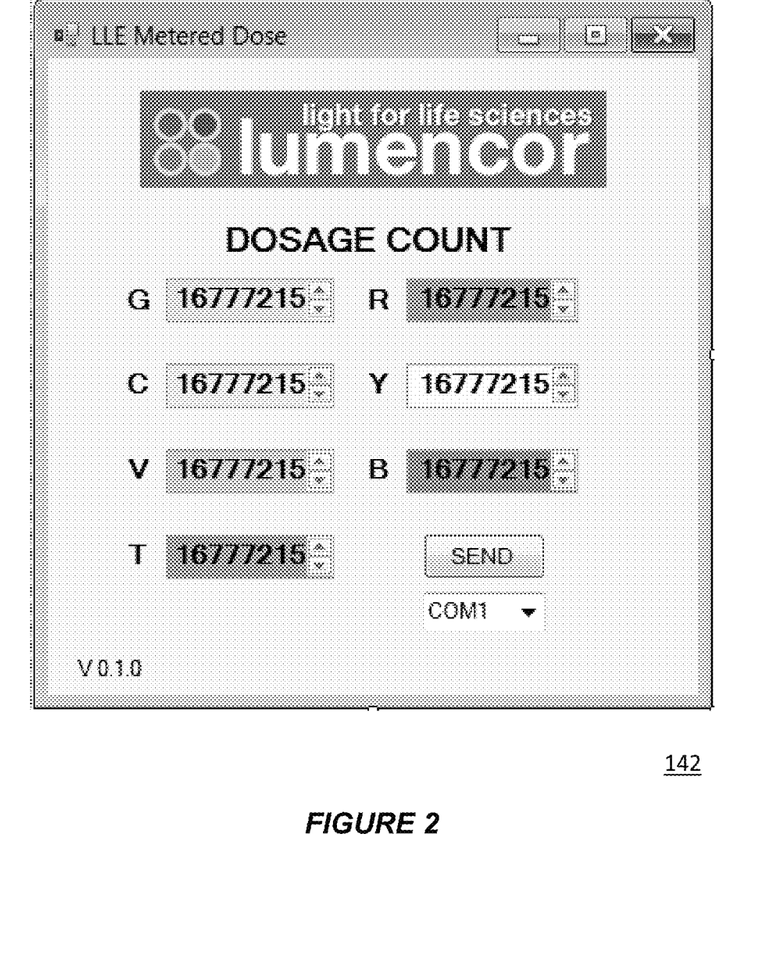
FIG. 2 illustrates an example of a graphical user interface (GUI), for use with a system for metered dosage illumination, in accordance with an embodiment.

FIG. 2 illustrates an example of a graphical user interface (GUI) 142, for use with a system for metered dosage illumination, in accordance with an embodiment. As shown in the example of FIG. 2, the GUI allows an operator to set and to monitor dosage counts in each of the plurality of colors that can be provided by the light engine.

Figure 3:
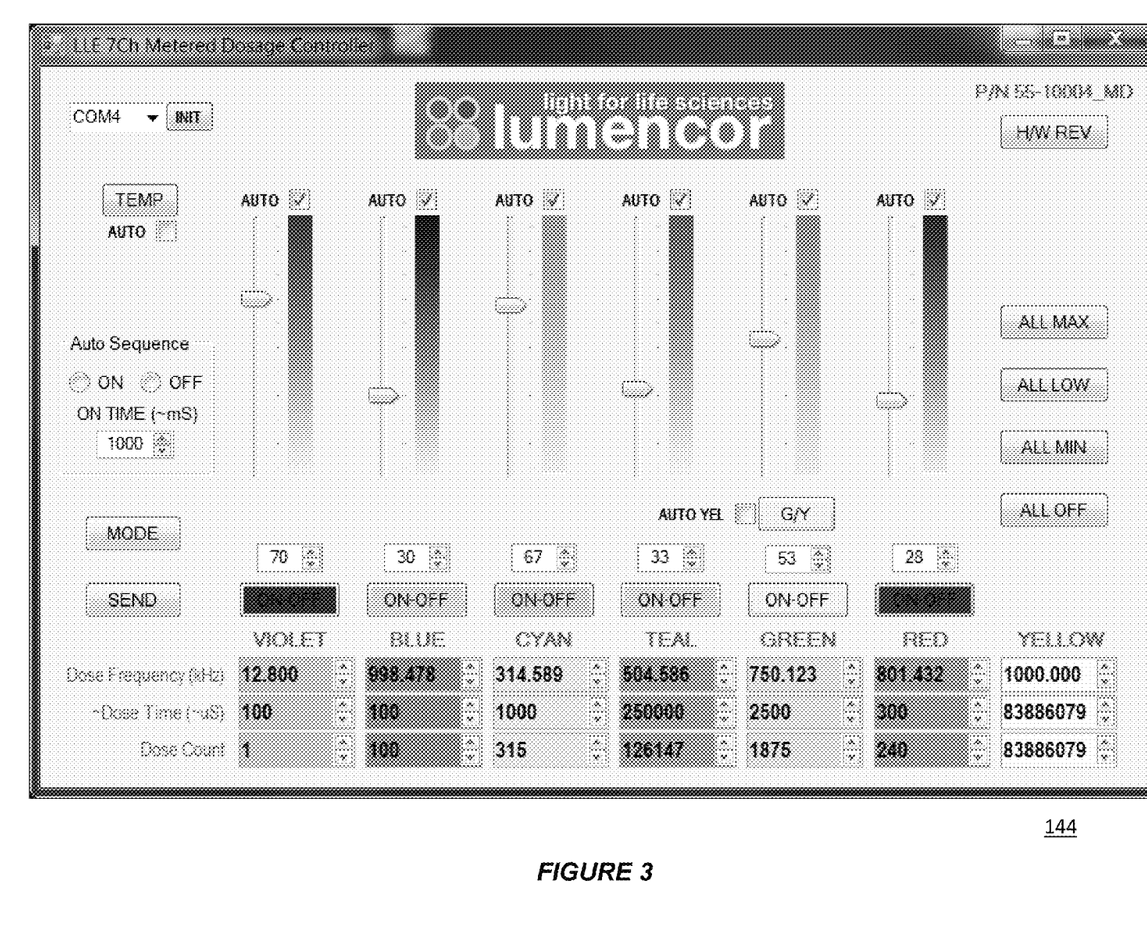
FIG. 3 illustrates an example of an alternative graphical user interface (GUI), for use with a system for metered dosage illumination, in accordance with an embodiment.

FIG. 3 illustrates an example of an alternative graphical user interface (GUI) 144, for use with a system for metered dosage illumination, in accordance with an embodiment. In the example shown in FIG. 3, the GUI controls power levels and exposure times. For each color channel, the operator can enter the relative power levels, maximum dosage frequency and approximate exposure period. In accordance with an embodiment, the system, or software therein, calculates the required dosage or reference count by multiplying the frequency by the desired exposure time. The exposure time is approximate, since the intensity can change resulting in shorter or longer exposure periods, but still yielding the same metered dosage for each period. If the power level is reduced (for example, by half) the dosimeter frequency is similarly reduced by half assuming a linear response. For the same exposure period the calculated dosage is reduced by half.

Quantitative Analysis

In accordance with an embodiment of particular use in quantitivate analysis, the system can comprise a collection of color channels, wherein each color channel is used to provide the specific wavelength band needed to excite a specific fluorescence molecule as defined by the fluorescence absorption of the tag. In accordance with an embodiment, each color channel can comprise a solid state light source (e.g. an LED, laser, light pipe or other light source), a single band pass filter, and an electronic circuit to power the light source. Within the system, the channels can be combined using, e.g. dichroic mirrors, so that the light from each source travels the same optical path, which is required, e.g. in epifluorescence measurements.

In accordance with an embodiment, the control circuitry can use a photodiode to measure the excitation light flux from each channel during each exposure period. An example of such a photodiode can be the TAOS light-to-frequency converter (part number TSL230RD), which can be used to quantify the light flux or dosage for each illumination pulse. The converter circuit generates pulses at a rate that is proportional to the light flux. Counting the pulses yields a measure of the dosage during each exposure time. Since dosage measurements can be made for each color channel independently, the user can optimize the amount of light, using a GUI such as that described above, to irradiate any given fluor uniquely. This allows for differences in efficiencies of all the processes involved in fluorescent signal generation to be taken into account for each color channel, (e.g. efficiency of light generation, fluorescence generation, or various differences in biological sample condition and fluor concentration).

In accordance with an embodiment, quantitative fluorescent measurements can be obtained ratiometrically by measuring the fluorescent signal, and dividing that signal by the dosage. In this manner, the fluorescent measurements can be normalized and rendered independent of the illumination intensity. This approach can be further automated by using dosage measurements to control the timing of the illumination and detection events. For example in accordance with an embodiment, a desired dosage count for each color channel can be entered into a reference counter. During a measurement, the control electronics monitor the dosage and gate off the excitation source for each color when the dosage count equals the amount in the reference counter. Light is metered independently of the exposure time period, rather as a function of the total light delivery prescribed by the reference counter. The precise dosage is delivered during each exposure, leading to quantitation as precise as the light flux measurement.

In this way, quantitative analysis can be performed using metered dosage with or without constant exposure times. In the former case, the light flux is maintained at the same level, and the flux is delivered within the exposure period. After the metered light dosage has been delivered, the excitation light is gated off leaving a time period when the camera can still detect fluorescent signals. In the latter case, the light flux is held constant, and the exposure time will vary as the intensity fluctuates.

In accordance with an embodiment, a range of light levels can be monitored and measured using conventional counters and logic circuitry. In some instances, the dosage levels may be so small as to generate insufficient statistical counts or too large and can overflow the counters. In these instances, a programmable gain can be used to dynamically adjust the count rate from the dosimeter circuitry.

Temporally Fast Analysis

In accordance with an embodiment of particular use in temporally fast analysis, the sources and circuitry can be implemented for fast switching, as is common with LEDs, lasers and light pipes. For example, in accordance with these embodiments, all switching can be performed electronically, with no mechanical motion. This allows modulation in the range of 10 ns to 1 ms to be readily achieved. In addition, significant speed increases can be achieved by directly connecting the camera and the illumination subsystem. In accordance with this embodiment, the host computer can trigger the camera to begin the analysis. The camera in turn can send a trigger to the illumination subsystem to turn on the excitation light. When the dosage count equals the reference count, the light is gated off, and a signal is sent to the camera to end the exposure. This configuration eliminates the variability in timing associated with non-real-time operating systems.

The illumination subsystem can also be used as a direct connection to drive the camera to activate or advance. Color channels can be programmed, e.g. via a ring buffer, to engage camera operation uniquely for each fluor of interest, each excitation source in a preprogrammed series of exposures of the various color channels. The timing of such camera and/or illuminator pulses can be optimized to interrogate specialized fluor characteristics, such as for fluorophor lifetime measurements, photoactivation and photolysis measurements as examples.

Photo-Bleaching and Phototoxicity

In accordance with another embodiment, the ability to precisely meter the light dosage and precisely turn on and off the illumination can minimize overall the exposure of the biological sample to the illuminator's excitation light. In so doing, photo-bleaching and phototoxicity effects are reduced, sample viability for live cell analyses is prolonged, and artifacts imposed by the lighting on the measurement are reduced. The combined benefit of such dosage optimization is enhanced accuracy and longer duration quantitative fluorescent analyses.

Modulation Techniques

Figure 4:
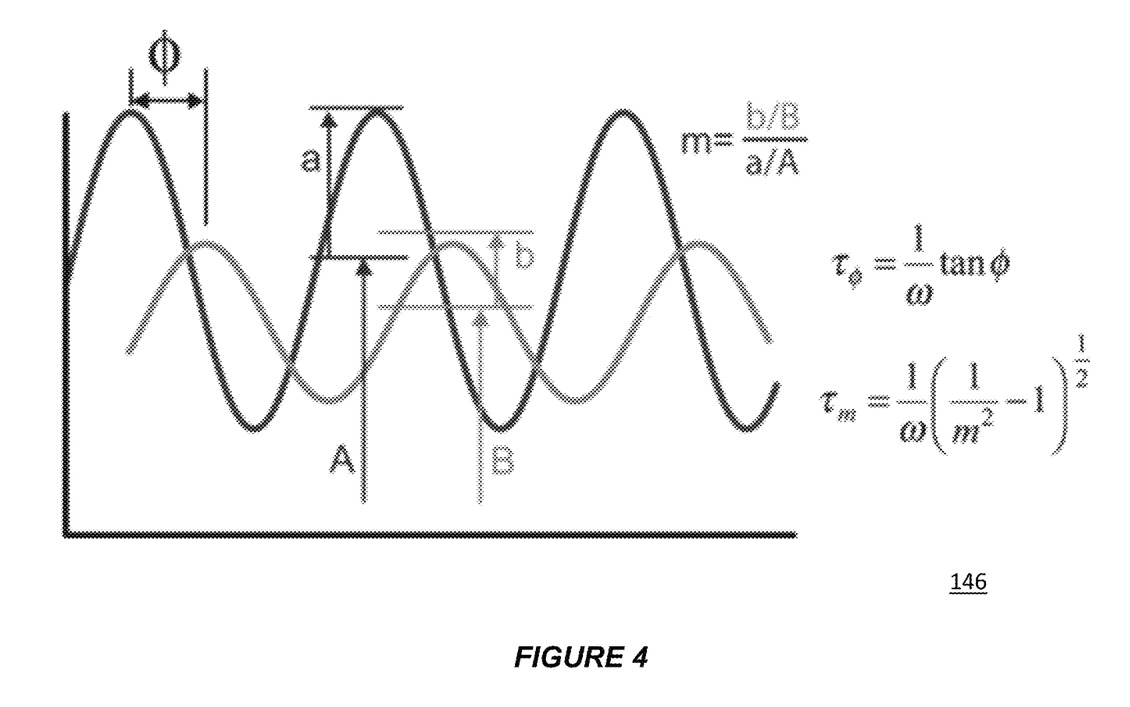
FIG. 4 illustrates an example of a fluorescence lifetime imaging microscopy (FLIM) technique, in accordance with an embodiment.

As described above, in accordance with an embodiment, a metered dosage technique can be used to obtain pulse-to-pulse repeatability and increase dynamic range. This technique involves gating the light on and off for the required dosage during each camera exposure period. Other modulation techniques can be used, e.g., Förster (or Fluorescence) Resonance Energy Transfer (FRET); or fluorescence lifetime imaging microscopy (FLIM), wherein the illumination is modulated, and the fluorescence lifetime is determined by the phase shift and modulation depth of the fluorescence signal relative to the illumination signal. FIG. 4 illustrates an example of a fluorescence lifetime imaging microscopy (FLIM) technique 146, in accordance with an embodiment.

Analog Measurement Techniques

Figure 5:
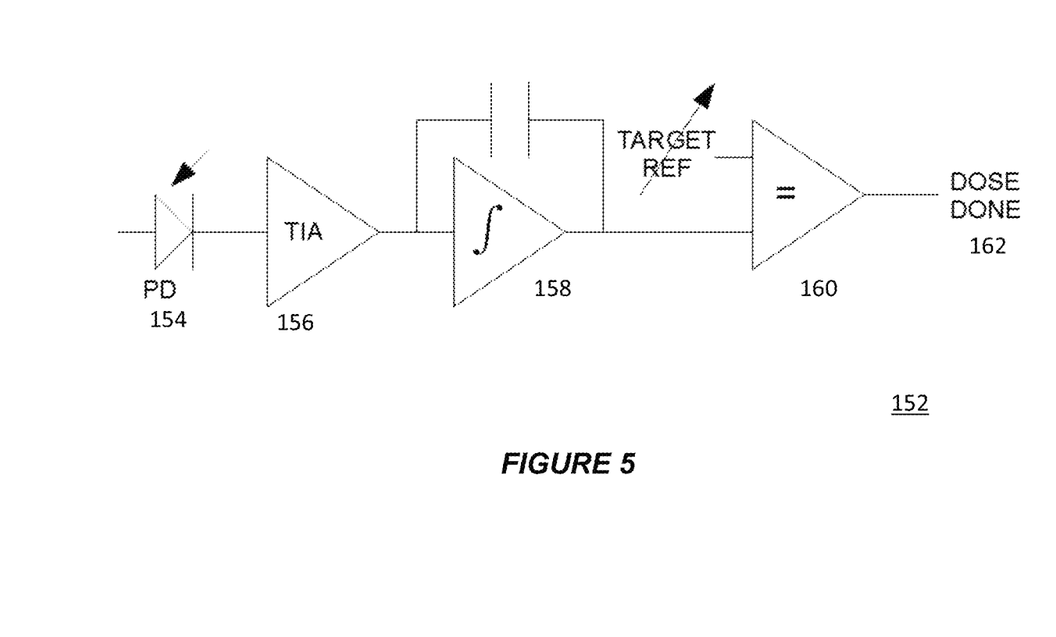
FIG. 5 illustrates an embodiment of an analog measurement of dosage, in accordance with an embodiment.

As described above, in accordance with an embodiment, a host computer can be used to generate an analysis protocol, including providing a dosage for each of the plurality of colors, and receiving feedback data from a camera, while a microprocessor-based counter counts the pulse train, and compares the ongoing count to the reference count or preset dosage for each color. In accordance with other embodiments, alternative measurement techniques, such as analog measurement techniques can be used. FIG. 5 illustrates an embodiment 152 which provides an analog measurement of dosage, in accordance with an embodiment. As shown in FIG. 5, the current output of a photodiode (PD) 154 can be fed to a transimpedance amplifier (TIA) 156, and converted to a voltage. This voltage signal can be integrated by the integrator opamp ($\int$) 158. The comparator (=) 160 compares the integrator output to a target reference level equal to the desired dosage. When the two values are the same, the comparator can generate a signal 162, turning off the light engine.

Use Cases

In accordance with an embodiment, the light engine can be operated in different modes, i.e. the output of the light engine can be controlled using a variety of different mechanisms, to satisfy particular use cases. This enables the light engine to be particularly useful in, e.g. quality-control, analysis, or assessment-based environments.

For example, although some light engines might provide an open loop option, in which output power information is readable on a monitor, such information is generally not fed back to any controller internal to the light engine. Although the current may be constant, there is no feedback mechanism on the power delivered, so the outputs are susceptible to a variety of atmospheric changes. In accordance with an embodiment, the use of a closed-loop option is beneficial not only for controlling inter-assay reproducibility, but also for monitoring inter-instrument reproducibility. For example, using a metered dosage approach, an entity can calibrate all of their light engines for all instrument products to deliver the same output power at a particular setting.

As another example, in analytical and clinical testing facilities, applications such as bioassay development, quality control in assay development and reagent formulation, clinical screening, diagnostics, treatment and therapeutic evaluation, and other analytical and bioanalytical endeavors, require that intra-assay control, as well as inter-instrument control, be robust and reproducible. This ensures that multiple instruments (e.g., readers, scanners and hand held analysis tools) processing the same or similar analyses will yield equivalent results in terms of the signal generated for similarly performed procedures. In turn, this requires the instrument performance itself to be well behaved and reproducible, which can only be accomplished in light-dependent bioanalytical equipment if the illumination can be controlled and identical for all instruments. In accordance with an embodiment, a metered dosage approach can be used to enable this type of quality control. In particular, the output of each instrument can be calibrated to, e.g. a NIST traceable standard, and the dosage required to achieve this power level can be recorded. Then, this identical light flux dosage, or an amount proportional to this dosage, can be delivered for each exposure for each instrument, or among different instruments within a family of analysis tools.

Use Case—Constant Current

In accordance with an embodiment, in a constant current mode, the light engine's circuitry monitors the current through each light source and keeps that constant. The amount of current can be sensed by measuring a voltage drop across a calibrated resistor. Once thermalized, the power output is constant for a constant ambient temperature and pressure, and the pulse-to-pulse reproducibility is better than 99%. This is a suitable option in a well-controlled environment with no thermal changes or warm up times. However, outputs can fluctuate as a function of warm up, duty cycle, power level and atmospheric conditions.

Figure 6:
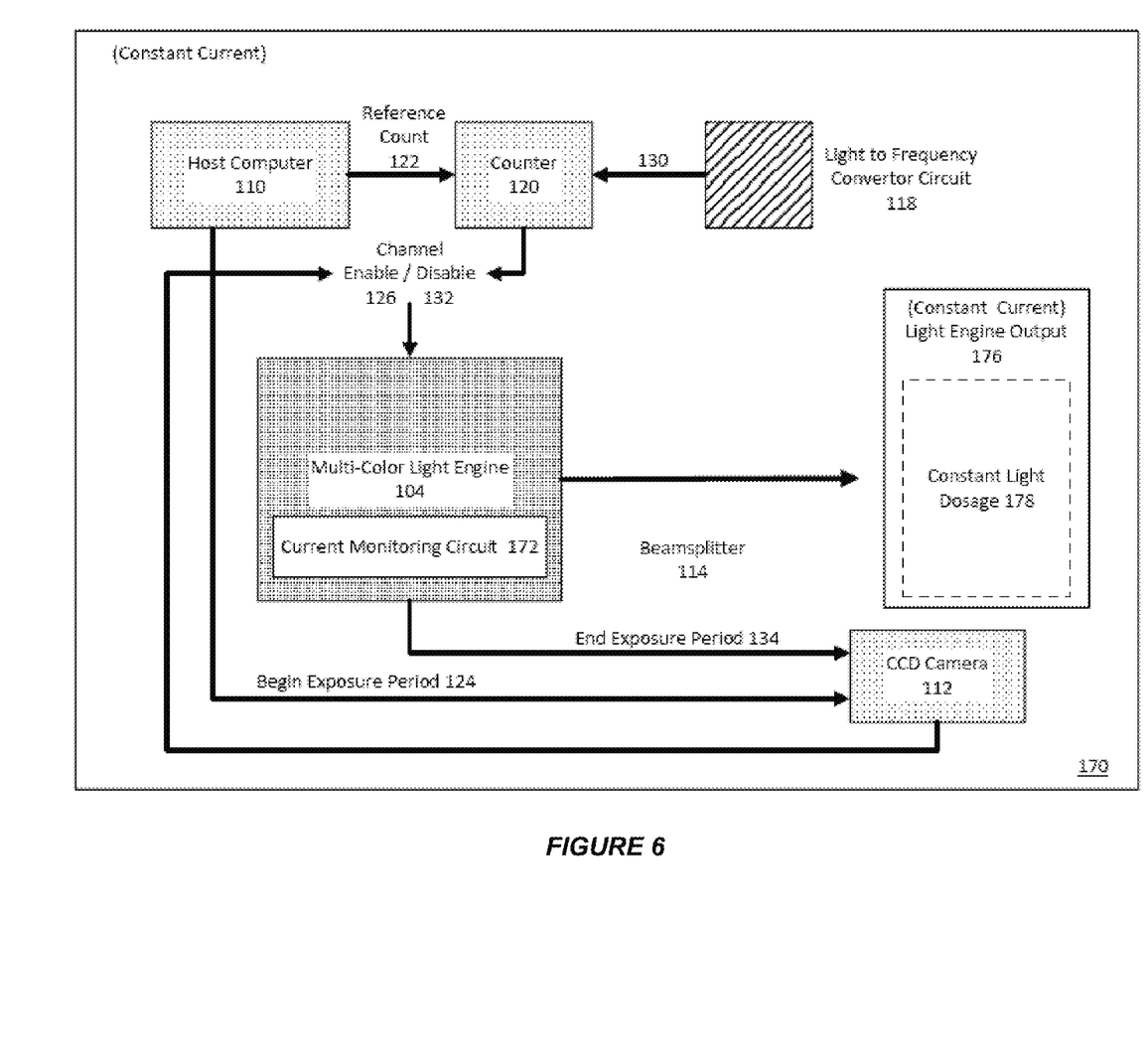
FIG. 6 illustrates how the system can be used to provide constant current dosage illumination, in accordance with an embodiment.

FIG. 6 illustrates how the system can be used to provide constant current dosage illumination, in accordance with an embodiment. As shown in FIG. 6, the system 170 can be provided similarly to that shown in FIG. 1 above. When a constant current mode is used, the light engine's current monitoring circuit 172 monitors the current through each light source and keeps that constant, to provide a constant current light output 176 of generally constant dosage 176 (subject to the considerations of warm up, duty cycle, power level and atmospheric conditions, as described above).

Use Case—Metered Dosage

In accordance with an embodiment, in a metered dosage mode, the system monitors a portion of the light engine output beam, internal to the light engine, using a light-to-frequency converter or circuitry, similar to that described above. The output of this circuitry is a pulse train which is fed to a counter. When the counter reaches the desired count or dosage, the light exposure is terminated. The total integrated light flux or dosage can be regulated to be the same for each camera exposure or defined detection period. This means that, although the time period that the light source is on may vary slightly, the number of counts does not. The output can be locked into the photon number, and the resultant dosage is not susceptible to warm up time, duty cycle, power level or changes in atmospheric conditions.

Figure 7:
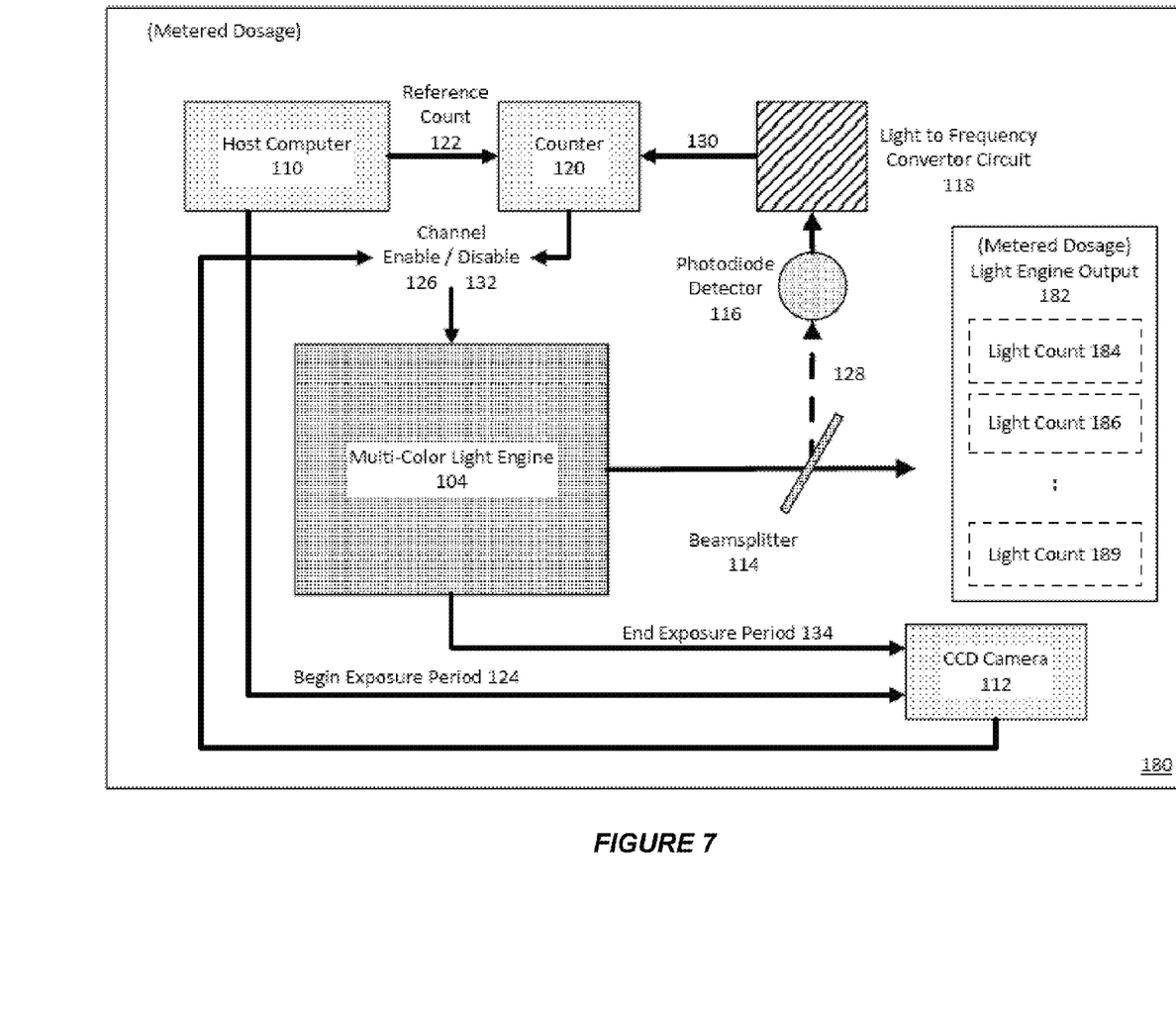
FIG. 7 illustrates how the system can be used to provide metered dosage illumination, in accordance with an embodiment.

FIG. 7 illustrates how the system can be used to provide metered dosage illumination, in accordance with an embodiment. As shown in FIG. 7, the system 180 can again be provided similarly to that shown in FIG. 1 above. When a metered dosage mode is used, the system monitors a portion of the light engine output beam, internal to the light engine, using a light-to-frequency converter or circuitry, and regulates the light output 182 to be the same count 184, 186, 189 for each camera exposure or defined detection period, so that, although the time period that the light source is on may vary slightly, the number of counts does not.

Use Case—Constant Intensity

In accordance with an embodiment, in a constant intensity mode, the light engine can include a circuitry that monitors the light output, and adjusts the intensity levels in real time. This mode is particularly useful in rolling shutter camera applications. Limitations of this approach versus, e.g. the metered dosage approach described above, include that there may be a compromise in the maximum power or intensity deliverable because some headroom is needed in order to offset the anticipated fluctuations; exposure times will generally be longer; and the dynamic range of the final instrument will be smaller than that for an instrument controlled by metered dosage. The accuracy of the light engine calibration will also be somewhat lower than that for metered dosage, because the sensor response will fluctuate due to atmospheric conditions.

Figure 8:
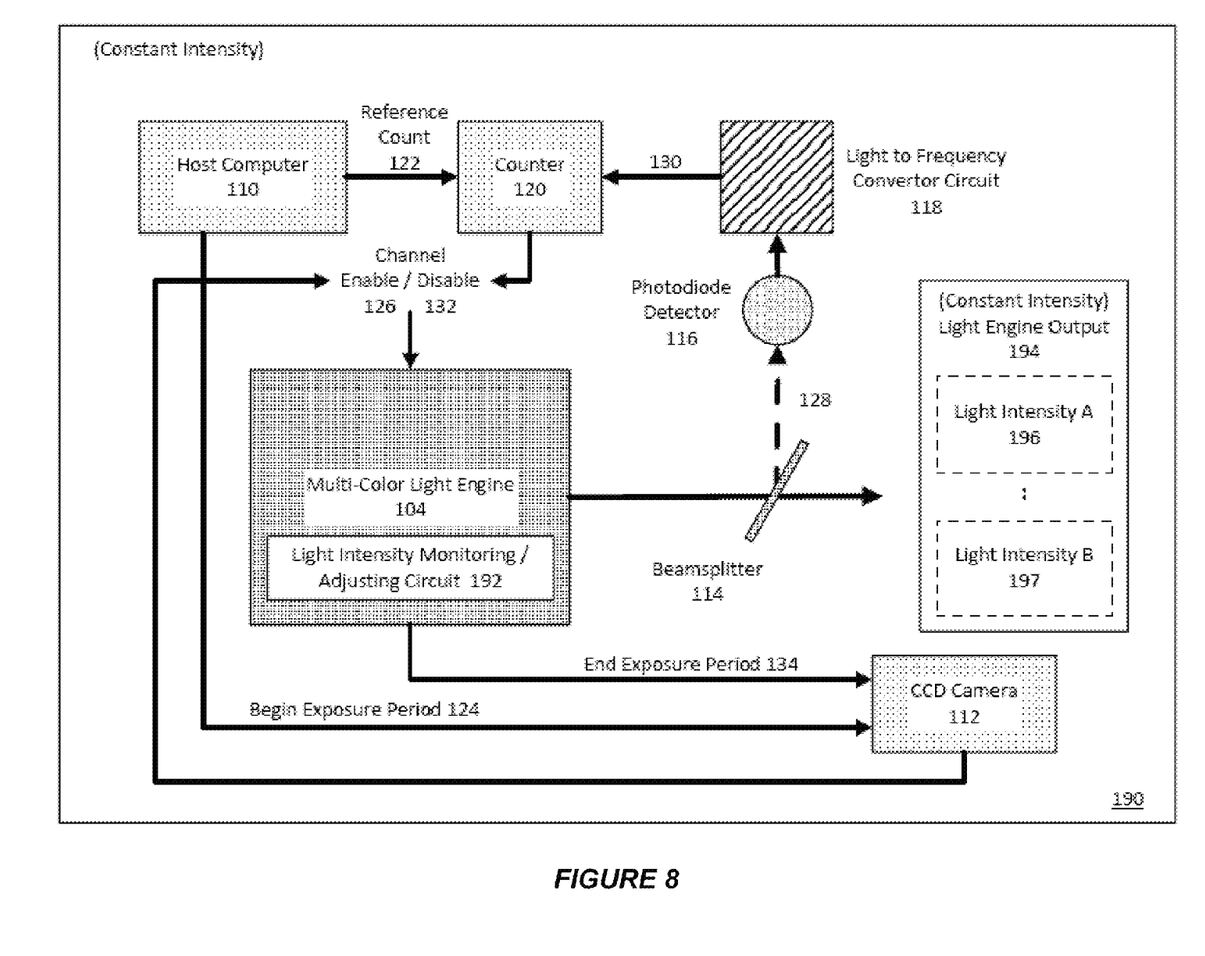
FIG. 8 illustrates how the system can be used to provide constant intensity illumination, in accordance with an embodiment.

FIG. 8 illustrates how the system can be used to provide constant intensity illumination, in accordance with an embodiment. As shown in FIG. 8, the system 190 can again be provided similarly to that shown in FIG. 1 above. When a constant intensity mode is used, a light intensity monitoring/adjusting circuit 192 monitors the light output 194, and adjusts the intensity levels of one or more sources 196, 197 in real time.

The present invention may be conveniently implemented using one or more conventional general purpose or specialized digital computers or microprocessors programmed according to the teachings of the present disclosure. Appropriate software coding can readily be prepared by skilled programmers based on the teachings of the present disclosure, as will be apparent to those skilled in the software art.

In some embodiments, the present invention includes a computer program product which is a storage medium (media) having instructions stored thereon/in which can be used to program a computer to perform any of the processes of the present invention. The storage medium can include, but is not limited to, any type of disk including floppy disks, optical discs, DVD, CD-ROMs, microdrive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data.

The foregoing description of the present invention has been provided for the purposes of illustration and description. It is not intended to be exhaustive or to limit the invention to the precise forms disclosed. In particular, although most of the examples above illustrate the providing of metered dosage illumination in the context of a bioanalysis system, the techniques can be similarly used to provide metered dosage illumination in the context of other types of systems. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A system for providing light to illuminate a sample comprising:
    a light engine including a plurality of color channels wherein each color channel includes,
        a solid state light source,
        a band pass filter, and
        an electronic circuit to power the solid state light source,
        whereby each color channel provides light of a different specific wavelength band suitable for exciting a fluorescent molecule;
    an optical system comprising a plurality of reflective elements internal to the system which direct light from each color channel into a light beam;
    a beam splitter which splits said light beam into an output light beam for illuminating said sample and a redirected light beam internal to the system;
    a light to frequency converter internal to the system which receives said redirected light beam from the beam splitter and generates a pulse train having a frequency proportional to an intensity of said redirected light beam;

a counter that maintains a count of pulses in the pulse train such that the count of pulses provides a measure of the intensity of light in said redirected light beam; and a light intensity circuit which monitors the ongoing count of pulses maintained by the counter and adjusts one or more of the plurality of color channels in real time to thereby control intensity of said output light beam for illuminating the sample.

2. The system of claim 1, wherein said plurality of color channels comprises at least four color channels selected from violet, blue, cyan, teal, green, red, and yellow, such that each of the four color channels provides light of a selected intensity and a different specific wavelength band suitable for exciting a fluorescent molecule, and wherein the plurality of color channels includes at least four solid state light sources and at least four band pass filters.

3. The system of claim 1, wherein said plurality of color channels comprises at least five color channels selected from violet, blue, cyan, teal, green, red, and yellow, such that each of the five color channels provides light of a selected intensity and a different specific wavelength band suitable for exciting a fluorescent molecule, and wherein the plurality of color channels includes at least five solid state light sources and at least five band pass filters.

4. The system of claim 1, further comprising:
a camera for measuring fluorescence received from a sample in response to exposure of the sample to the output light beam.

5. The system of claim 1, further comprising:
a camera for measuring fluorescence received from a sample in response to exposure of the sample to the output light beam; and
a host computer for triggering an exposure period of said camera.

6. The system of claim 1, wherein the light intensity circuit monitors the ongoing count of pulses maintained by the counter and adjusts one or more of the plurality of color channels in real time to thereby maintain constant output light beam intensity.

7. The system of claim 1, wherein the system is used as part of a bioanalysis system.

8. The system of claim 1, wherein the system is used as part of a bioanalysis system used for detection of fluorescent molecules in a biological sample.

9. The system of claim 1, wherein the system is used as part of a bioanalysis system for one or more of: quantitative analyses, temporally fast analyses, fluorescence imaging, gene expression analysis, sequencing, high resolution fluorescence microscopy, fluorescence life time measurements, Förster Resonance Energy Transfer (FRET) Microscopy, and high content screening.

10. A method comprising:
providing a light engine including a plurality of color channels, wherein each color channel includes, a solid state light source, a band pass filter, and an electronic circuit to power the solid state light source, and whereby each color channel provides light of a different specific wavelength band suitable for exciting a fluorescent molecule;
causing one or more of the color channels to provide light of a different specific wavelength band suitable for exciting a fluorescent molecule;
combining the light from each of the plurality of color channel into a light beam using a plurality of reflective elements;
splitting the light beam using a beamsplitter into a redirected light beam directed at a light to frequency converter internal to the light engine and an output light beam for illuminating a sample;
receiving the redirected light beam from the beam splitter with a light to frequency converter;
generating a pulse train with said light to frequency converter wherein the pulse train has a frequency proportional to an intensity of light in said redirected light beam;
maintaining a count of pulses in the pulse train such that the count of pulses provides a measure of the intensity of light in said redirected of the light beam; and
adjusting one or more of the plurality of color channels in real time in response to the count of pulses to thereby control intensity of said output light beam for illuminating the sample.

11. The method of claim 10, wherein the plurality of color channels includes at least four color channels selected from violet, blue, cyan, teal, green, red, and yellow, such that each of the four color channels provides light of a different specific wavelength band suitable for exciting a fluorescent molecule, and wherein the plurality of color channels includes at least four solid state light sources and at least four band pass filters.

12. The method of claim 10, wherein the plurality of color channels includes at least five color channels selected from violet, blue, cyan, teal, green, red, and yellow, such that each of the five color channels provides light of a different specific wavelength band suitable for exciting a fluorescent molecule, and wherein the plurality of color channels includes at least five solid state light sources and at least five band pass filters.

13. The method of claim 10, further comprising:
directing the output light beam at a sample; and
measuring fluorescence received from a sample in response to exposure of the sample to the output light beam.

14. The method of claim 10, further comprising:
directing the output light beam at a sample;
triggering an exposure period of a camera;
using the camera to measure fluorescence received from the sample in response to exposure of the sample to the output light beam.

15. The method of claim 10, wherein said adjusting step comprises adjusting one or more of the plurality of color channels in real time in response to the count of pulses to thereby maintain constant output light beam intensity.

16. The method of claim 10, further comprising:
directing the output light beam at a sample; and
measuring fluorescence received from the sample in response to exposure of the sample to the output light beam to perform analysis of said sample.

17. The method of claim 10, further comprising:
directing the output light beam at a biological sample; and
measuring fluorescence received from the biological sample in response to exposure of the biological sample to the output light beam to detect fluorescent molecules in the biological sample.

18. The method of claim 10, further comprising:
directing the output light beam at a sample; and
measuring fluorescence received from the sample in response to exposure of the sample to the output light beam to perform analysis of said sample wherein said analysis includes one or more of: quantitative analyses, temporally fast analyses, fluorescence imaging, gene expression analysis, sequencing, high resolution fluorescence microscopy, fluorescence life time measurements, Förster Resonance Energy Transfer (FRET) Microscopy, and high content screening.

19. A system for the detection of fluorescent molecules in a biological sample, the system comprising:
- a light engine including a plurality of color channels wherein each color channel includes,
  - a solid state light source,
  - a band pass filter, and
  - an electronic circuit to power the solid state light source, whereby each color channel provides light of a different specific wavelength band suitable for exciting a fluorescent molecule;
- an optical system comprising a plurality of reflective elements which direct light from each color channel into a light beam;
- a beam splitter which splits the light beam internal to the system into a redirected beam and an output light beam;
- a light to frequency converter which receives said redirected light beam from the beam splitter internal to the system and generates a pulse train having a frequency proportional to an intensity of light in said redirected light beam;
- a counter that maintains a count of pulses in the pulse train such that the count of pulses provides a measure of the intensity of light in said redirected light beam;
- a light intensity circuit which monitors the ongoing count of pulses maintained by the counter and adjusts one or more of the plurality of color channels in real time to thereby control intensity of the output light beam; and
- a camera for measuring fluorescence received from the sample in response to exposure of the biological sample to the output light beam.

20. The system of claim 19, further comprising a host computer which triggers said light engine and triggers said camera.

21. The system of claim 19, wherein the plurality of color channels comprises at least four color channels selected from violet, blue, cyan, teal, green, red, and yellow, such that each of the four color channels provides light of a selected intensity and a different specific wavelength band suitable for exciting a fluorescent molecule, and wherein the plurality of color channels includes at least four solid state light sources and at least four band pass filters.

22. The system of claim 19, wherein the system is used as part of a bioanalysis system for one or more of: quantitative analyses, temporally fast analyses, fluorescence imaging, gene expression analysis, sequencing, high resolution fluorescence microscopy, fluorescence life time measurements, Förster Resonance Energy Transfer (FRET) Microscopy, and high content screening.

* * * * *